(12) United States Patent
Riesinger (10) Patent No.: US 9,387,130 B2
(45) Date of Patent: Jul. 12, 2016

(54) METHOD FOR INCREASING THE SKIN OR WOUND COMPATIBILITY OF A CELLULOSE NONWOVEN FABRIC

(75) Inventor: Birgit Riesinger, Ostbevern (DE)

(73) Assignee: BSN medical GmbH, Hamburg (DE)

( * ) Notice: Subject to any disclaimer, the term of this patent is extended or adjusted under 35 U.S.C. 154(b) by 0 days.

(21) Appl. No.: 13/997,367

(22) PCT Filed: Sep. 30, 2011

(86) PCT No.: PCT/EP2011/067186
§ 371 (c)(1),
(2), (4) Date: Aug. 13, 2013

(87) PCT Pub. No.: WO2012/045690
PCT Pub. Date: Apr. 12, 2012

(65) Prior Publication Data
US 2013/0312234 A1    Nov. 28, 2013

(30) Foreign Application Priority Data
Oct. 6, 2010   (DE) .......................... 10 2010 038 006

(51) Int. Cl.
| | |
|---|---|
| D06C 3/06 | (2006.01) |
| D06C 15/00 | (2006.01) |
| D06C 19/00 | (2006.01) |
| D04H 1/28 | (2012.01) |
| D04H 1/44 | (2006.01) |
| A61F 13/15 | (2006.01) |
| D04H 1/26 | (2012.01) |

(52) U.S. Cl.
CPC ..... *A61F 13/15658* (2013.01); *A61F 13/15707* (2013.01); *D04H 1/26* (2013.01); *D04H 1/28* (2013.01); *D04H 1/44* (2013.01); *D06C 3/06* (2013.01); *D06C 19/00* (2013.01); *D06C 15/00* (2013.01)

(58) Field of Classification Search
CPC .......... D06C 3/06; D06C 15/00; D06C 15/08; D06C 19/00; D06C 27/00; D04H 1/44; D04H 1/28; D04H 1/26; D04H 1/407; D04H 1/425; D04H 17/10; D04H 17/12; A61F 13/15707; A61F 13/15658
USPC .......................... 26/19, 22, 25, 27, 99; 28/165
See application file for complete search history.

(56) References Cited

U.S. PATENT DOCUMENTS

| | | | | | |
|---|---|---|---|---|---|
| 2,705,497 | A | * | 4/1955 | Johnson et al. | 604/365 |
| 3,408,709 | A | * | 11/1968 | Reitz | 26/51 |
| 3,592,732 | A | * | 7/1971 | Wand | 162/197 |
| 3,738,128 | A | * | 6/1973 | Sando | D06C 15/00 68/22 R |
| 4,631,788 | A | * | 12/1986 | Dischler | D06C 19/00 26/25 |
| 4,769,879 | A | * | 9/1988 | Otto | B29C 59/04 26/25 |
| 4,857,065 | A | * | 8/1989 | Seal | 604/368 |

(Continued)

FOREIGN PATENT DOCUMENTS

WO    WO 2010026251 A1 *  3/2010 ............. A61F 13/00

*Primary Examiner* — Amy Vanatta
(74) *Attorney, Agent, or Firm* — Rankin, Hill & Clark LLP (57) ABSTRACT

The invention relates to a method for increasing the skin or wound compatibility of a hygiene or wound care product, which has a cellulose nonwoven fabric and which is present in the form of a web, or of a precursor product of said hygiene or wound care product. The product is stretched and deviated in at least one direction in such manner that the cohesion of fibers or flakes of the cellulose nonwoven fabric is weakened, reduced, disrupted, or broken down at least in some sections.

7 Claims, 8 Drawing Sheets

(56) References Cited

U.S. PATENT DOCUMENTS

| | | | | |
|---|---|---|---|---|
| 5,167,054 | A * | 12/1992 | Eschenbach | 26/27 |
| 5,413,811 | A * | 5/1995 | Fitting | D04H 1/54 156/164 |
| 5,445,777 | A * | 8/1995 | Noel | A61F 13/15658 264/113 |
| 5,543,215 | A * | 8/1996 | Hansen et al. | 442/417 |
| 2004/0044322 | A1 * | 3/2004 | Melius | A61F 13/15658 604/385.01 |
| 2004/0051199 | A1 * | 3/2004 | Kellenberger et al. | 264/166 |
| 2008/0217809 | A1 * | 9/2008 | Zhao et al. | 264/229 |
| 2011/0184365 | A1 * | 7/2011 | Rottger et al. | 604/372 |
| 2011/0213286 | A1 * | 9/2011 | Riesinger | 602/43 |
| 2012/0064298 | A1 * | 3/2012 | Orr | A61F 13/15707 428/156 |
| 2012/0276238 | A1 * | 11/2012 | Strube et al. | 425/336 |
| 2012/0276341 | A1 * | 11/2012 | Lake et al. | 428/174 |

\* cited by examiner

METHOD FOR INCREASING THE SKIN OR WOUND COMPATIBILITY OF A CELLULOSE NONWOVEN FABRIC

The invention relates to a method according to the preamble of claim 1.

Absorbent materials are particularly well suited for use in absorbent disposable articles, for example, diapers, incontinence inserts and the like, because they are resilient but firm and allow the wearer great freedom of movement in daily life.

A material of this type that is commonly used in absorbent disposable articles is a cellulose nonwoven fabric which comprises cellulose fibers or flakes that adhere to each other on their surfaces. Therefore, there is a higher risk of the material losing its integrity in a nonwoven than, for example, in the case of woven or knitted fabrics in which the fibers are firmly connected to each other. Accordingly, the aim of manufacturing nonwovens always has always been to achieve as high as possible a cohesion of the fibers or flakes, at least in the dry state of the nonwoven.

From DE69813027, a method is known for producing such a nonwoven. However, it has been observed that this nonwoven, when used in wound dressings is associated with low wearer comfort—in particular low skin or wound compatibility.

SUMMARY OF THE INVENTION

Therefore, the problem of the present invention is to provide a hygiene or wound care product that does not have the mentioned disadvantages of the products of the prior art.

The main problem of the invention is to provide a method that allows an increase of the skin or wound compatibility of a cellulose nonwoven fabric.

These problems are solved with a hygiene or wound care product according to the present main claim; the dependent claims indicate preferred embodiments. The value ranges delimited by numerical values are always understood to include the mentioned numerical values.

DETAILED DESCRIPTION OF THE INVENTION

According to the invention, a method is provided for increasing the skin or wound compatibility of a hygiene or wound care product, which has a cellulose nonwoven fabric and which is present in the form of a web, or of a precursor product thereof, wherein the product is pulled and deviated in at least one direction, in such a manner that the cohesion of the fibers or flakes of the cellulose nonwoven is weakened, reduced, disrupted, or broken down at least in some sections.

The term "cellulose nonwoven fabric" denotes a textile fabric made of individual cellulose fibers, which is not produced from yarns, in contrast to woven fabrics, crocheted fabrics, and knitted fabrics. A nonwoven fabric thus consists of loosely combined fibers that are not connected to each other. The strength of a nonwoven fabric is based only on inherent fiber adherence. The latter can be influenced by reworking, for example, by expanding, kneading, compressing, or drawing. This is due to the fact that reworking decreases the adherence of the fibers to each other, as a result of which the nonwoven fabric overall loses strength. Nonwoven fabrics are also referred to as "nonwovens" or "airlaids," and they are produced, for example, by fulling the fibers.

Below, the term "form of a web" denotes the two- or three-dimensional form of the cellulose nonwoven fabric. It is in the form of a width of material, as a flat material of unchanging width and height (thickness) which can be wound or unwound. Naturally, the width and the height can vary depending on the use; however they remain the same within one width of material.

Below, the term "pull" refers to the force that pulls the cellulose nonwoven fabric of a hygiene or wound care product, which is present in the form of a web, or a precursor product thereof. In other words, the pulling force in the cellulose nonwoven fabric of the hygiene or wound care product, which is present in the form of a web, or of a precursor thereof, acts in the direction from the attachment point to the force application point.

Below, the term "deviate" refers to the fact that the pull of the cellulose nonwoven material of a hygiene or wound care product, which is present in the form of a web, or of a precursor product thereof, extends not horizontally or in a level manner; instead the cellulose nonwoven material is deviated at a certain angle in the longitudinal direction, or tilted in the transverse direction.

The hygiene or wound care product can correspond to the absorbent insert which is contained in a wound dressing of the applicant of the present invention, as disclosed, for example, in WO03094813, WO2007051599, and WO0152780, and marketed under the commercial name "sorbion sachet." The disclosure content of the mentioned documents is included in its entirety in the disclosure content of this document.

In another embodiment, the hygiene or wound care product can also form a core which comprises—optionally flake shaped—fibers or yarns made of superabsorbent polymers as well as of superabsorbent polymers in granulate form, where the granulates are glued or welded to the fibers or yarns at several heights, and the granulates are distributed over more than 50% of the entire design height of at least one section of the core, wherein mixed regions of granulate and fibers exist. Here, the weight proportion of the superabsorbent polymers can preferably be in the range of 10-25 wt %. Similar constructions are known from conventional incontinence materials, and, like hygiene diapers, they are known for their padding properties. A sheath can be arranged around the mentioned core; it can be arranged with overlap in some areas, covering, for example, a gluing seam, or forming a portion thereof.

In another embodiment, the hygiene or wound care product can also contain at least one flat layer comprising fibers or yarns made of superabsorbent polymers, to which superabsorbent polymers in granulate form are glued. As a result, in a preferred embodiment, a structure is obtained which comprises at least three layers, wherein two cover layers surround a layer comprising superabsorbent polymers. Here, there is preferably no mixing of fibers and superabsorbent polymers in the plane; instead, the two materials are only in a fixed adjacent arrangement.

Below, the term "precursor product" denotes a preliminary stage of the hygiene or wound care product. In particular, in the case of the use of the hygiene or wound care product in a special application, for example, in negative pressure therapy, the method according to the invention is carried out on a preliminary stage of the hygiene or wound care product proper, which is subsequently processed further.

It was observed surprisingly that such a method which weakens, reduces, disrupts, or breaks down the cohesion of fibers or flakes of the cellulose nonwoven fabric at least in some sections, increases the skin or wound compatibility of a hygiene or wound care product, which has a cellulose nonwoven fabric and which is present in the form of a web, or of the precursor product thereof.

Figure 6:
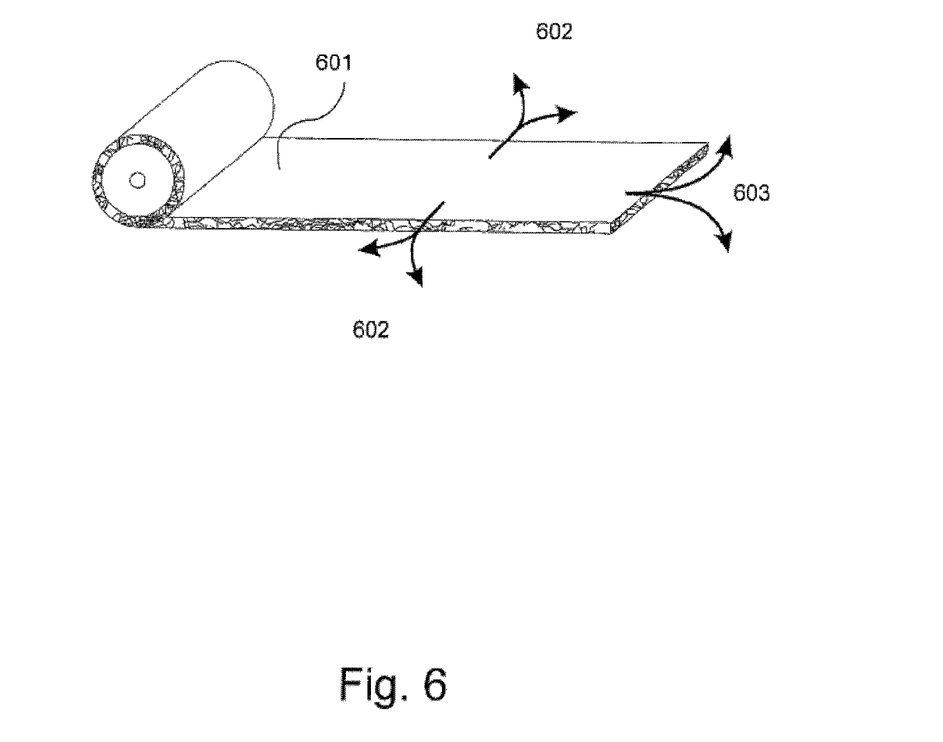
FIG. 6 diagrammatically shows a precursor product of a hygiene or wound care product 601, which is present in the form of a web, and which is deviated in two directions 602 and 603.

It is preferable for the hygiene or wound care product or the precursor product thereof to be deviated in two or more directions (see FIG. 6).

In a further embodiment of the method according to the invention, the method reduces the stiffness of the hygiene or wound care product, which is present in the form of a web, or of a precursor product thereof.

This occurs by reducing or loosening the cohesion of the fibers, for example, by expanding, kneading, compressing or drawing, sufficiently so that the cellulose nonwoven fabric of a hygiene or wound care product, which is present in the form of a web, or of the precursor product thereof, is no longer felt to be stiff.

This embodiment is particularly advantageous for a precursor product of a hygiene or wound care product, which is present in the form of a web, or for the precursor product thereof, which is to be used in a wound dressing, since it is characterized by high softness and snugness, and thus by a high wearer comfort.

In a further embodiment of the method according to the invention, the hygiene or wound care product or the precursor product thereof is guided over at least one deviating roller pair.

Below, the term "deviating roller" refers to a roller which is mounted with as little friction as possible on an axle. It is used for guiding the cellulose nonwoven fabric of a hygiene or wound care product, which is present in the form of a web, or of the precursor product thereof. The deviating roller is attached in such a manner that it does not change its position during utilization, but can in principle be adjusted.

This step is advantageous because it makes it possible, in a particularly efficient manner—cost effectively and using a simple production technology—to weaken, reduce, disrupt, or break down the cohesion of the fibers or flakes of a cellulose nonwoven fabric at least in some sections, as a result of which the cellulose nonwoven fabric is loosened, and thus its skin or wound compatibility is increased.

Preferably, at the margin of the deviating roller, there is a delimitation which prevents the sliding off of the cellulose nonwoven fabric of a hygiene or wound care product, which is present in the form of a web, or of the precursor product thereof.

Deviating rollers are known, for example, from calendering processes in which the material is guided over several deviating rollers or cylinders—a so-called calender. Depending on the arrangement of the cylinders and of the material feed one distinguishes between I, L, F and Z calenders. Furthermore, calenders can solidify nonwoven materials made of thermoplastic polymers to nonwoven fabrics.

Figure 1:
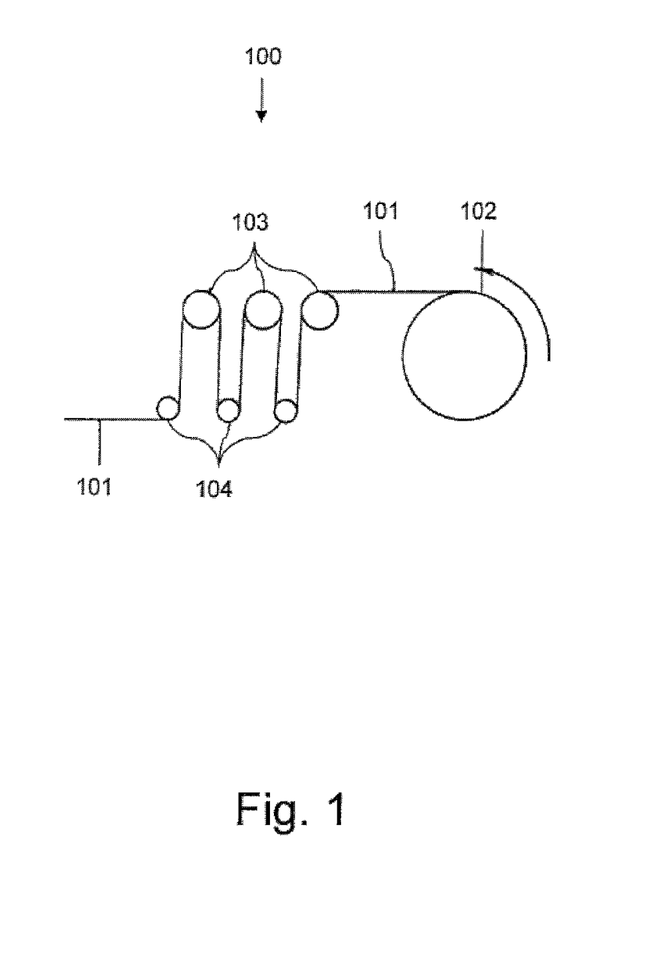
FIG. 1 diagrammatically shows an embodiment of the method 100 according to the invention.

The deviation of the hygiene or wound care product or of the precursor product thereof preferably occurs via the deviating roller in the longitudinal direction (see FIG. 1, for example).

Here, it is particularly preferable to provide that the pulling rate, the radii of the deviating rollers, and the angle of rotation established by the arrangement of the deviating rollers are selected in such a manner that the cohesion of fibers or flakes of the cellulose nonwoven fabric is weakened, reduced, disrupted, or broken down at least in some sections.

| Parameter | Effect |
| --- | --- |
| Radius of the deviating roller | The smaller, the stronger the loosening effect |
| Pulling rate | The higher, the stronger the loosening effect |
| Winding and unwinding angle | The greater, the stronger the loosening effect |

Figure 7:
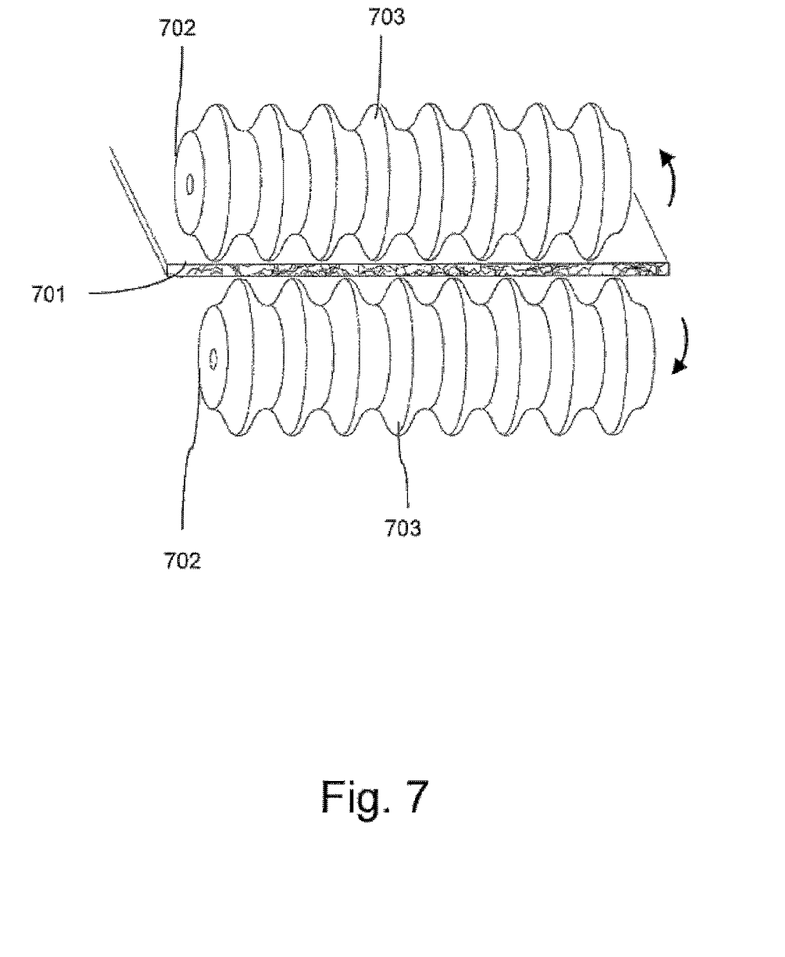
FIG. 7 diagrammatically shows a precursor product of a hygiene or wound care product 701, which is present in the form of a web, and, in more detail than in FIG. 4, two deviating rollers 702 provided with circumferential ridges 703.

In a further embodiment of the method according to the invention, the hygiene or wound care product or the precursor product thereof is guided over at least one deviating roller provided with circumferential ridges (see FIG. 7).

This is advantageous, since said ridges can form a wave structure on the deviating roller, which further decreases the cohesion of the fibers or flakes of the cellulose nonwoven fabric and thus further increases the skin or wound compatibility of the cellulose nonwoven fabric.

Here, it is particularly preferable to provide that the pulling rate, the radius and the height of the deviating roller, the distance between the deviating rollers, and the shape of the ridges are selected in such a manner that the cohesion of fibers or flakes of the cellulose nonwoven fabric are weakened, reduced, disrupted, or broken down.

Moreover, it is preferable that the deviation of the hygiene or wound care product or of the precursor product thereof occurs in the transverse direction.

This deviation can represent the only deviation present, but it can of course also be combined with the deviation in the longitudinal direction.

An additional deviation is advantageous, since, as a result, the cohesion of the fibers or flakes of the cellulose nonwoven material is further reduced, the nonwoven becomes looser, and thus the skin or wound compatibility of the cellulose nonwoven fabric is increased.

Here it is particularly preferable to provide that the pulling rate, the radii of the deviating rollers, and the angle of rotation established by the arrangement of the deviating rollers are selected in such a manner that the cohesion of the fibers or flakes of the cellulose nonwoven material is weakened, reduced, disrupted, or broken down at least in some sections.

| Parameter | Effect |
| --- | --- |
| Radius of the deviating roller | The smaller, the stronger the loosening effect |
| Pulling rate | The higher, the stronger the loosening effect |
| Height of the ridge | The greater, the stronger the loosening effect |

In a further embodiment of the method according to the invention, the hygiene or wound care product or the precursor product thereof is guided over a fulling station with at least one roller comprising fulling punches.

Below, the term "fulling station" below denotes a device by means of which the hygiene or wound care product or the precursor product thereof is guided. Here, the fulling punches of the fulling station (see FIG. 8) act on the hygiene or wound care product or on the precursor product thereof—they knead it—as a result of which the cellulose nonwoven fabric of the hygiene or wound care product, which is present in the form of a web, or of the precursor product thereof, is loosened at least partially. Said fulling punches can be spring mounted.

Here, it is particularly advantageous to provide that the pulling rate, the diameter, and the height of the fulling punches are selected in such a manner that the cohesion of fibers or flakes of the cellulose nonwoven fabric is weakened, reduced, disrupted, or broken down.

It is preferable for the deviation of the hygiene or wound care product, which is present in the form of a web, or of the precursor product thereof to occur in all directions, particularly in the longitudinal and in the transverse directions.

In a preferred embodiment of the method according to the invention, the hygiene or wound care product or the precursor product thereof is fed to a cutting and/or sheathing station.

Below, the term "sheathing station" denotes a device which sheathes the hygiene or wound care product or the precursor product thereof with a lamination, a film, etc.

The sheathing can be from different materials on the two sides.

Below, the term "cutting station" denotes a device which trims the hygiene or wound care product or the precursor product thereof to the desired size.

The cutting and/or sheathing station preferably contains a device for closing or securing the sheathing, for example, by sewing or welding.

This step can take place before the first step, between different steps, or after the last step of the method according to the invention.

In a further embodiment of the method according to the invention, the hygiene or wound care product or the precursor product thereof, for the purpose of increasing the skin or wound compatibility, is pulled out of or from a storage device prior to the first step.

Said storage device is preferably a supply roll (see FIG. 1).

This step is advantageous, because, in combination with the already mentioned steps, it enables the fully automatic manufacture of a hygiene or wound care product with increased skin or wound compatibility.

In a further embodiment of the method according to the invention, the hygiene or wound care product or the precursor product thereof is perforated, embossed and/or stamped at least in some sections.

This step is advantageous because, in this manner, for example, the absorption capacity of the hygiene or wound care product or of the precursor product thereof can be changed.

In a further embodiment of the method according to the invention, the hygiene or wound care product or the precursor product thereof is provided with a linear embossing in its marginal area.

It is preferable here to provide a peripheral embossing in the marginal area. The aim of said embossing is to prevent the exit of material (for example, cellulose fibers and/or flakes), which is mobilized in the step(s) for increasing the skin or wound compatibility, from the hygiene or wound care product.

This design makes sense particularly if, in the previous process steps for increasing the skin or wound compatibility, the cohesion of fibers or flakes of the cellulose nonwoven material is weakened, reduced, disrupted, or broken down only in an inner region of the hygiene or wound care product or of the precursor product thereof. Said embossing in the marginal area then acts like a seal which can prevent the exit of the mobilized material if applicable.

In a further embodiment of the method according to the invention, the hygiene or wound care product, which is present in the form of a web, has a multilayered structure.

In a further embodiment of the method according to the invention, the hygiene or wound care product, which is present in the form of a web, comprises superabsorbent polymers.

Below, the term "superabsorbent polymers" denotes plastics that are capable of absorbing liquids in amounts that are a multiple—up to 1000 times—of their own weight. Chemically they consist of a copolymer of acrylic acid (propenoic acid, $C_3H_4O_2$) and sodium acrylate (acrylic acid sodium salt, $NaC_3H_3O_2$), wherein the ratio of the two monomers to each other can vary. In addition, a so-called core cross-linker (CXL) is added to the monomer solution, which links the produced long-chain polymer molecules in some sections to each other by chemical bridges (it "crosslinks"). As a result of these bridges, the polymer becomes water insoluble. When water or aqueous liquids penetrate into the polymer particle, the latter particle swells, tightening said network on a molecular level, so that the water can no longer escape without assistance.

The superabsorbent polymers (SAP) can be in the form of a bulk product, wherein the term "bulk product" can cover both granulates and powders and also pieces of material, such as foam pieces.

The superabsorbent particles can be in the form of powders or granulates having a particle size between 10 and approximately 5000 μm.

However, in the case of superabsorbent polymers, the fiber form is also particularly preferable, since the product in this case a very soft product both in the dry and in the swollen state, which can be modeled and which is not stiff, and which, in addition, has a low abrasiveness in contrast to the absorbent polymers that are present in granulate or powder form. This applies both to fibers and also to knitted, matted or nonwoven fabrics and/or fiber wadding.

The mentioned properties make superabsorbent polymers in fiber form particularly suitable for products according to the invention which are designed as patient bedding mats and decubitus pillows. It is precisely in such fields of application that high softness is particularly important.

In a further embodiment of the method according to the invention, the hygiene or wound care product, which is present in the form of a web, has a weight per unit area ranging from 20 to 100 $g/m^2$ inclusive.

In a further embodiment of the method according to the invention, the hygiene or wound care product, which is present in the form of a web, has a thickness from 0.7 to 60 mm inclusive.

In a further embodiment of the method according to the invention the hygiene or wound care product, which is present in the form of a web, has a ratio of Gurley stiffness (mg) to density (g/cm$^2$) between 100 and 5000 inclusive.

The term "Gurley stiffness" denotes a test method which measures the bending resistance of a material. The method is carried out, for example, according to TAPPI Method T 543 om-94, and is measured in milligrams; Here, a mean determined from 5 samples is frequently indicated.

DRAWINGS

FIG. 1 diagrammatically shows an embodiment of the method 100 according to the invention. The precursor product of a hygiene or wound care product 101, which is present in the form of a web, is drawn in the direction of the arrow out of or from a storage device 102, here a nonwoven web roll, and fed to a first deviating roller 103. The deviating rollers bearing the reference numeral 103 all have the same diameter or radius. In the first deviating roller 103, the cellulose nonwoven fabric 101 is deviated at a certain angle and pulled in the direction of a second deviating roller 104. The deviating rollers bearing the reference numeral 104 all have the same diameter or radius. As a result of the repeated deviation at certain angles over deviating rollers having different diameters and as a result of the predetermined pulling rate at which the method is implemented, one achieves that the cohesion of fibers or flakes of the cellulose nonwoven fabric 101 is weakened, reduced, disrupted, or broken down at least in some sections.

In general it is true that the smaller the radius of a deviating roller 103, 104 is, the higher the pulling rate is, and the higher the winding and unwinding angle of the cellulose nonwoven fabric 101 on a deviating roller 103, 104 is, the more strongly the cohesion of fibers or flakes of the cellulose nonwoven fabric 101 is weakened, reduced, disrupted, or broken down at least in some sections.

Figure 2:
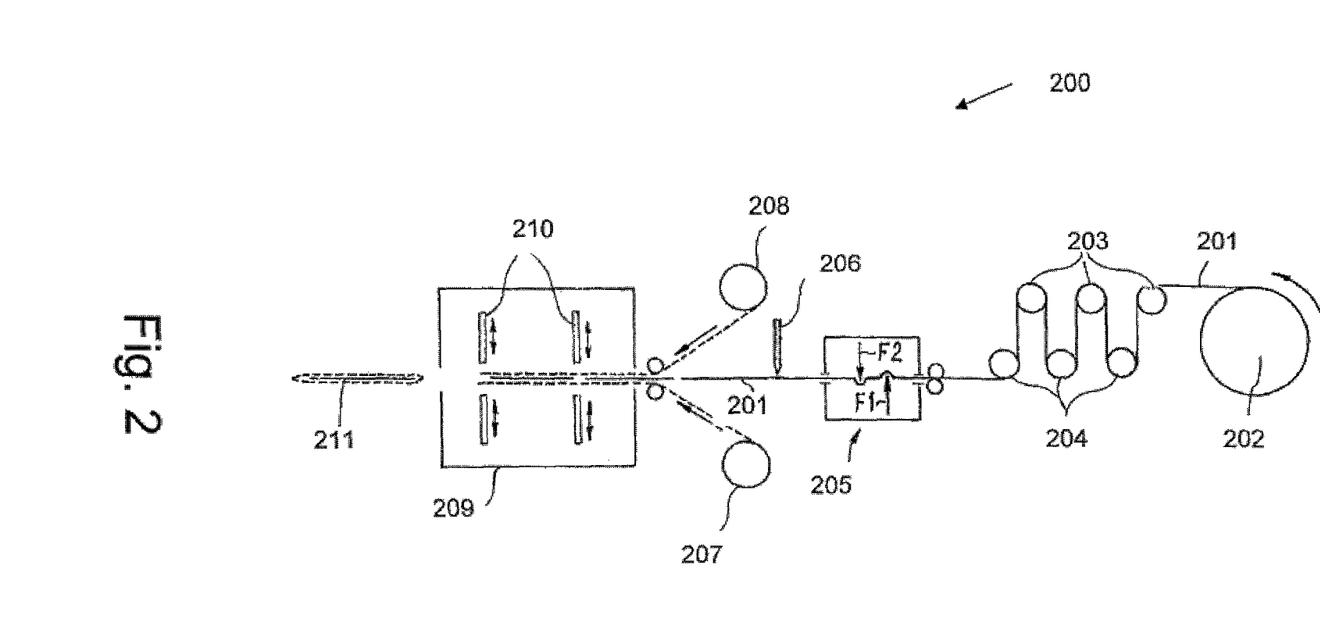
FIG. 2 diagrammatically shows an additional embodiment of the method 200 according to the invention.

FIG. 2 diagrammatically shows a further embodiment of the method according to the invention 200. Again, a precursor product of a hygiene or wound care product 201, which is present in the form of a web, is pulled in the direction of the arrow out of or from a storage device 202, here a cellulose nonwoven fabric roll, and fed to a first deviating roller 203. The deviating rollers bearing the reference numerals 203 are all arranged along an axis. In this example, all the deviating rollers have the same diameter or radius. On the first deviating roller 203, the nonwoven web 201 is deviated at a certain angle and pulled in the direction of a second deviating roller 204. The deviating rollers bearing the reference numeral 204 are all arranged along an axis. After the cellulose nonwoven fabric 201 has passed the deviating rollers 203, 204, it is guided over deviating rollers with circumferential ridges 205 which form a wave structure on the deviating roller. As a result of the repeated deviation at certain angles over deviating rollers, of the predetermined pulling rate at which the method is implemented, and of the guiding over deviating rollers with circumferential ridges, one achieves that the cohesion of fibers or flakes of the cellulose nonwoven fabric 201 is weakened, reduced, disrupted, or broken down at least in some sections. Next, the cellulose nonwoven fabric 201 is cut up by a cutting tool 206 into sections of predetermined size. The resulting sections of the cellulose nonwoven fabric of a hygiene or wound care product, which is present in the form of a web, are subsequently sheathed in a sheathing station 209 with a sheathing made of two different materials 207 and 208, respectively, wherein the edges of the sheath, in this example, are welded with the ultrasound welding electrodes 210. The result of the method according to the invention is a hygiene or wound care product comprising a cellulose nonwoven fabric which has a very high skin or wound compatibility.

Figure 3:
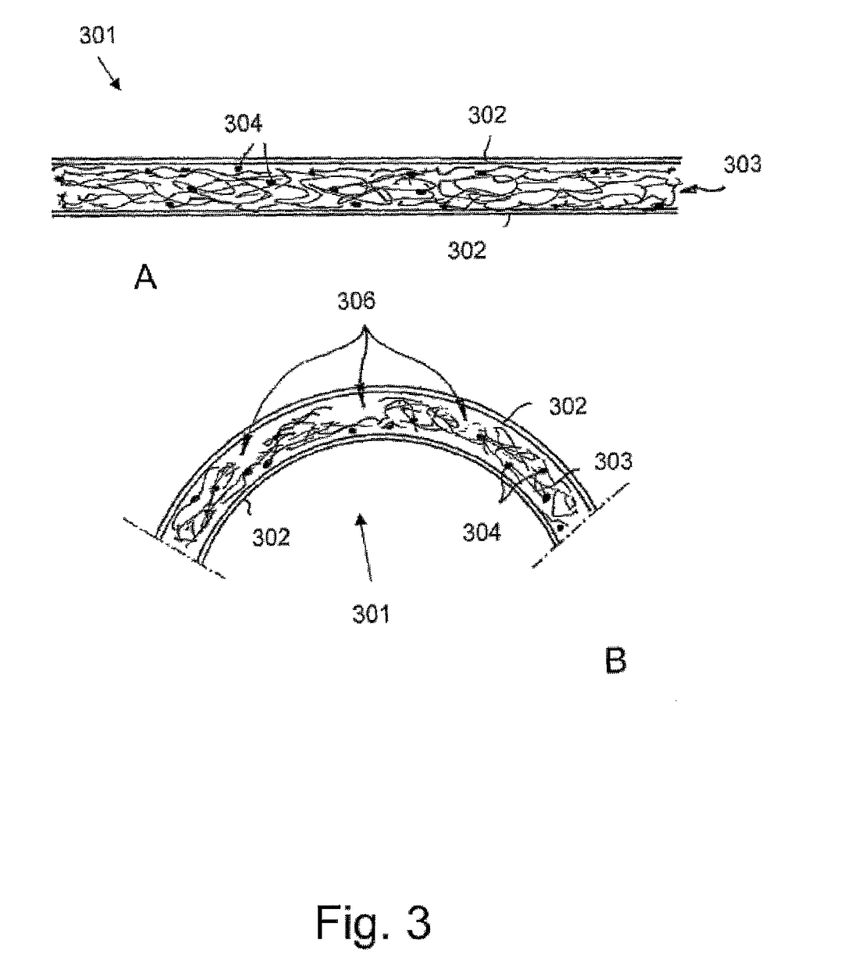
FIG. 3 diagrammatically shows a multi-layer hygiene and wound care product 301 in the form of a web, comprising a nonwoven cover layer 302, a core layer 303, and superabsorbent particles 305 before (FIG. 3A) and after (FIG. 3B) implementation of the method according to the invention.

FIG. 3 diagrammatically shows a multi-layer hygiene or wound care product 301, which is present in the form of a web, comprising a nonwoven cover layer 302, a core layer 303, and superabsorbent particles 305 before (FIG. 3A) and after (FIG. 3B) implementation of the method according to the invention.

FIG. 3A diagrammatically shows that, before carrying out the method according to the invention, the multi-layer hygiene or wound care product 301, which is in the form of a web, is relatively stiff, since the fibers or flakes of the cellulose nonwoven fabric, in particular of the core layer 303, hold together firmly.

FIG. 3B diagrammatically shows that, after carrying out the method according to the invention, the multi-layer hygiene or wound care product 301, which is present in the form of a web, is much looser and more flexible, since the fibers or flakes, in particular of the core layer 303, have been weakened, reduced, disrupted, or broken down at least in some sections 306. The resulting cellulose nonwoven web 301 thus has a very high skin or wound compatibility.

Figure 4:
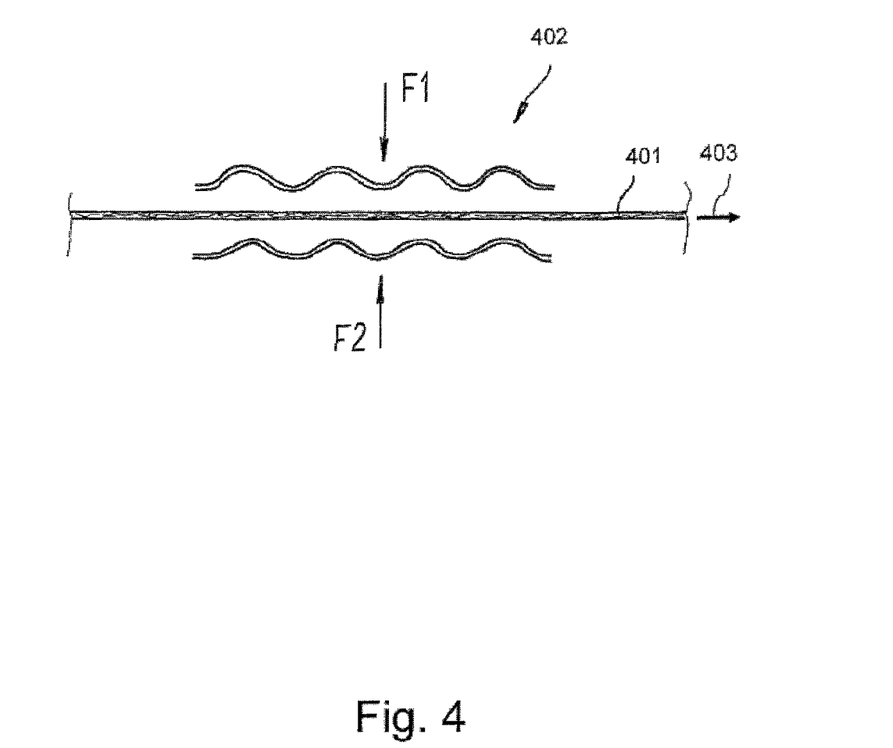
FIG. 4 diagrammatically shows a precursor product of a hygiene or wound care product 401, which is present in the form of a web, and of deviating rollers with circumferential ridges 402.

FIG. 4 diagrammatically shows a precursor product of a hygiene or wound care product 401, which is present in the form of a web, and deviating rollers with circumferential ridges 402. When carrying out the method according to the invention, these deviating rollers with the circumferential ridges 402 are sufficiently close to each other so that the fibers or flakes of the cellulose nonwoven fabric of a hygiene or wound care product 401, which is present in the form of a web, are weakened, reduced, disrupted, or broken down by the forces F1 and F2 at least in some sections, while the cellulose nonwoven fabric of a hygiene or a wound care product 401, which is present in the form of a web, is guided in the pulling direction 403 over the deviating rollers with circumferential ridges 402.

Figure 5:
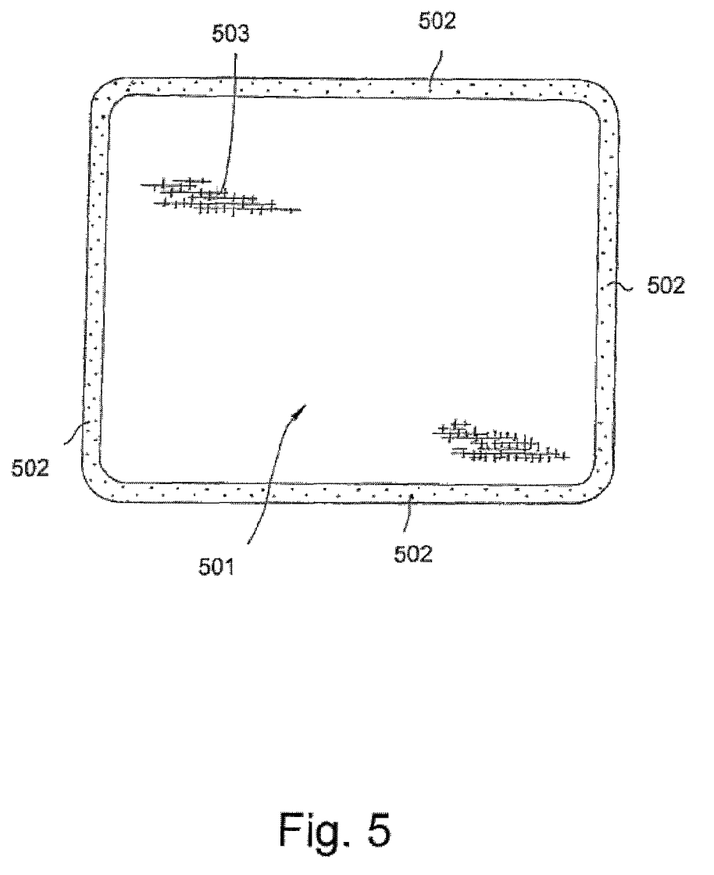
FIG. 5 diagrammatically shows a hygiene or wound care product 501, which is provided with a circumferential embossing 502 in its marginal area.

FIG. 5 diagrammatically shows a hygiene or a wound care product 501 which is provided with a peripheral embossing 502 in its marginal area. The aim of the embossing is to prevent material (particularly cellulose fibers and/or flakes), which has been mobilized in the step(s) for increasing the skin or wound compatibility, from being able to exit from the hygiene or wound care product 501. The mentioned embossing in the marginal area accordingly acts like a seal which can prevent an exit of the mobilized material 503 if applicable.

FIG. 6 diagrammatically shows that a precursor product of a hygiene or wound care product 601, which is present in the form of a web, is deviated in two directions 602 and 603. In this example, the deviation in the first direction 602 is equivalent to a tilting of the cellulose nonwoven fabric of a hygiene or wound care product 601, which is present in the form of a web, in the transverse direction, while the deviation in the second direction 603 corresponds to a change of the longitudinal direction.

The deviation in the transverse and longitudinal directions is advantageous, since, as a result, the cohesion of the fibers or flakes of the cellulose nonwoven fabric of the hygiene or wound care product 601, which is present in the form of a web, is decreased more strongly, and thus the nonwoven fabric becomes looser and consequently more skin tolerable and wound compatible, than when it is deviated only in one direction.

FIG. 7 diagrammatically shows a precursor product of a hygiene or wound care product 701, which is present in the form of a web, and, in more detail than in FIG. 4, two deviating rollers 702 provided with circumferential ridges 703. The circumferential ridges 703 form a wave structure on the deviating roller 702, by means of which the cohesion of the fibers or flakes of the cellulose nonwoven fabric of the hygiene or wound care product 701, which is present in the form of a web, is further decreased, and thus the skin or wound compatibility of the cellulose nonwoven fabric is increased more strongly than when the cellulose nonwoven fabric is guided only over deviating rollers. Here, it is true that the higher the circumferential ridges 703 are, the more strongly the cohesion of fibers or flakes of the cellulose nonwoven fabric is weakened, reduced, disrupted, or broken down at least in some sections.

Figure 8:
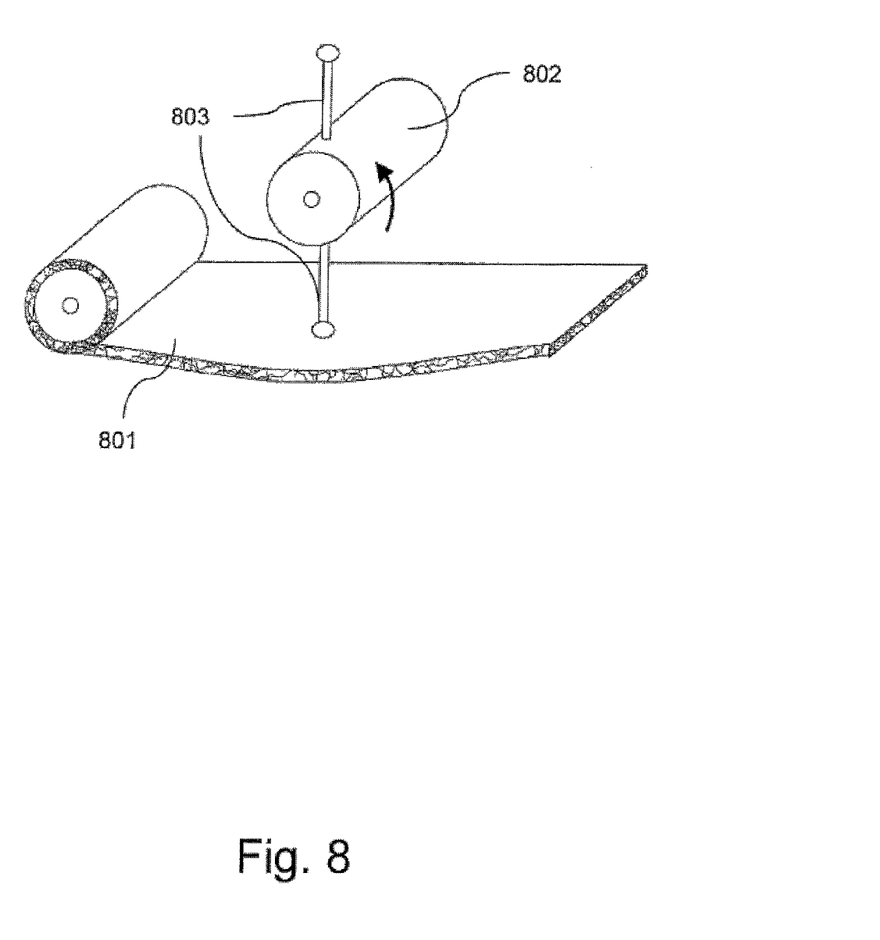
FIG. 8 diagrammatically shows a precursor product of a hygiene or wound care product 801, which is present in the form of a web, and a deviating roller or roller 802 with fulling punches 803.

FIG. 8 diagrammatically shows a precursor product of a hygiene or wound care product 801, which is present in the form of a web, and a deviating roller or roller 802 with fulling punches 803. When the cellulose nonwoven fabric 801 is guided over the fulling punches 803, during the implementation of the method according to the invention, the fulling punches 803 act on the cellulose nonwoven fabric of a hygiene or wound care product 801, which is present in the form of a web, as a result of which it is loosened at least partially.

LIST OF REFERENCE NUMERALS

| Feature | Reference numeral |
|---|---|
| Method according to the invention | 100, 200 |
| Cellulose nonwoven fabric of a hygiene or wound care product, which is present in the form of a web | 101, 201, 301, 401, 601, 701, 801 |
| Storage device | 102, 202 |
| Deviating roller | 103, 203 |
| Deviating roller | 104, 204 |
| Deviating rollers with circumferential ridges | 205, 402, 702, |
| Cutting tool | 206 |
| Sheathing material | 207 |
| Sheathing material | 208 |
| Sheathing station | 209 |
| Ultrasound welding electrodes | 210 |
| Nonwoven cover layer | 302 |
| Core layer | 303 |
| Superabsorbent particles | 305 |
| Sections of the cellulose nonwoven fabric with weakened or disrupted fibers | 306 |
| Pulling direction | 403 |
| Hygiene or wound care product | 501 |
| Peripheral embossing | 502 |
| Mobilized material | 503 |
| First deviation direction | 602 |
| Second deviation direction | 603 |
| Circumferential ridges | 703 |
| Deviating roller or roller with fulling punches | 802 |
| Fulling punches | 803 |

The invention claimed is:

1. A method for manufacturing a hygiene or wound care product having increased skin or wound compatibility, the method comprising:
providing a precursor product in a form of a web of cellulose nonwoven fabric that comprises individual cellulose fibers or flakes, and superabsorbent polymers; and
pulling and deviating the precursor product in at least one direction in such a manner that cohesion of the fibers or flakes of the web of cellulose nonwoven fabric is weakened, reduced, disrupted, or broken down at least in some sections, said pulling and deviating including at least
guiding the precursor product over a plurality of calender rollers to deviate the precursor product in a longitudinal direction, and
guiding the precursor product over at least one deviating roller provided with circumferential ridges to deviate the precursor product in a transverse direction; and
forming the hygiene or wound care product by sealing the pulled and deviated precursor product between two sheathing layers that are joined together via a peripheral embossing, wherein the two sheathing layers and peripheral embossing prevent material mobilized from the precursor product in the pulling and deviating step from exiting from the hygiene or wound care product.

2. The method according to claim 1, wherein the method reduces the stiffness of the hygiene or wound care product, or of the precursor product.

3. The method according to claim 1, wherein the method comprises guiding the precursor product over a fulling station with at least one roller comprising fulling punches.

4. The method according to claim 1, wherein the method further comprises feeding the hygiene or wound care product or the precursor product to a cutting station.

5. The method according to claim 1, wherein the method comprises perforating, embossing and/or stamping the precursor product at least in some sections.

6. The method according to claim 1, wherein the method comprises providing the hygiene or wound care product with a linear embossing in its marginal area.

7. The method according to claim 1, wherein the hygiene or wound care product has a ratio of Gurley stiffness (mg) to density (g/cm$^2$) ranging between 100 and 5000 inclusive.

* * * * *